US010339617B2

(12) United States Patent
Nessinger et al.

(10) Patent No.: US 10,339,617 B2
(45) Date of Patent: Jul. 2, 2019

(54) ORDER PROFILE SAFEGUARDING MECHANISM

(75) Inventors: Christopher Nessinger, Kansas City, MO (US); Charles F. Schneider, Kansas City, MO (US)

(73) Assignee: Cerner Innovations, Inc., Kansas City, KS (US)

( * ) Notice: Subject to any disclaimer, the term of this patent is extended or adjusted under 35 U.S.C. 154(b) by 3025 days.

(21) Appl. No.: 11/345,565

(22) Filed: Feb. 1, 2006

(65) Prior Publication Data
US 2007/0179807 A1   Aug. 2, 2007

(51) Int. Cl.
| G06Q 10/10 | (2012.01) |
| G06Q 50/22 | (2018.01) |
| G06Q 10/00 | (2012.01) |
| A61B 5/00  | (2006.01) |

(52) U.S. Cl.
CPC .......... G06Q 50/22 (2013.01); G06Q 10/10 (2013.01); G06Q 10/107 (2013.01)

(58) Field of Classification Search
CPC .............................. G06Q 10/00; G06Q 50/00
USPC ................................... 702/2, 3, 20; 705/2, 3
See application file for complete search history.

(56) References Cited

U.S. PATENT DOCUMENTS

| 7,552,223 B1* | 6/2009 | Ackaouy et al. ............. 709/229 |
| 7,831,642 B1* | 11/2010 | Kumaresan et al. ......... 707/822 |
| 7,831,977 B2* | 11/2010 | Shultz et al. ................. 718/104 |
| 2001/0018658 A1* | 8/2001 | Kim ................................... 705/1 |
| 2002/0120472 A1* | 8/2002 | Dvorak et al. ..................... 705/3 |
| 2005/0256818 A1* | 11/2005 | Sun .................. G06Q 10/06316 705/301 |
| 2007/0033073 A1* | 2/2007 | Tajaliawal et al. ............... 705/3 |
| 2007/0061266 A1* | 3/2007 | Moore et al. ................... 705/51 |

OTHER PUBLICATIONS

Reference A—Fuller, UNIX Programming, "Chapter Twelve—Semaphores, Messages, Queues and Shared Memory",http://snap.nlc.dcccd.edu/learn/fuller3/chap 12/chap 12.html, Copyright 2001 by James L. Fuller.*

* cited by examiner

*Primary Examiner* — Robert W Morgan
*Assistant Examiner* — Charles P Coleman
(74) *Attorney, Agent, or Firm* — Shook, Hardy & Bacon L.L.P.

(57) ABSTRACT

An order management system that employs profile locking is provided for managing clinical orders in patient profiles. The system allows users to initiate lockable order actions (e.g., order actions requiring a profile lock for conflict checking) in a profile locked by another user. When a user attempts to initiate a lockable order action, the system provides a notification to the user indicating that the patient profile is locked by another user. The user may elect to continue initiating the lockable order action. When the profile becomes available, the system provides a notification to the user, who may then obtain the profile lock and process the lockable order action, including having the system perform conflict checking. The system may also provide for the initiation of an instant messaging session between the user attempting to enter a lockable order action in a locked profile and another user who has the profile lock.

20 Claims, 6 Drawing Sheets

ORDER PROFILE SAFEGUARDING MECHANISM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

Healthcare orders are requests placed by healthcare providers, such as physicians and nurses, for example, for medication and non-medication tasks to be performed for a patient. An order may include, for instance, a request for a procedure, a medication, a laboratory test, an evaluation, a treatment, or a nursing task to be performed. A variety of electronic order management systems have been developed for clinical environments that allow healthcare providers to enter and manage orders for their patients. One example of such an electronic order management system is the POWERORDERS application available from Cerner Corporation of North Kansas City, Mo. For instance, using such an order management system, a physician wishing to prescribe a medication for a particular patient may access a profile for the patient and initiate an order for the medication, entering details for the medication order. After initiating the order, the physician may "sign" the order, indicating to the order management system to process the order. Once the order has been processed in the order management system, it is electronically dispersed to the appropriate location, such as a pharmacy, so that care can be administered based on the directives of that particular order. In addition, the order is maintained in the profile allowing other clinicians to view the order, as well as any other orders that have been placed for the patient.

Some electronic order management systems provide sophisticated features to assist healthcare providers in the care process. For instance, when a physician enters a medication order, a system may perform dose range checking to determine whether the dosage entered by the physician is appropriate. In addition, a system may determine and/or warn whether the patient has any allergies to the medication. Further, some systems perform conflict checking by comparing orders being entered against orders already within the profile to determine if a conflict exists. For example, a system may perform interaction checking to determine whether an adverse interaction exists between a medication order being entered and any medication orders currently within the profile. In addition, a system may perform duplicate checking to determine whether a medication order duplicates a current medication order for the patient.

To accurately perform conflict checking in which orders being entered are compared against existing orders within a profile, such as for interaction checking and duplicate checking, an order management system must have a static profile between the time of checking and the time the order is processed. For example, some systems allow multiple users to simultaneously access a profile and enter orders. If such a system were to perform interaction checking when a healthcare provider initiates a medication order, the system may miss interactions with any orders that are entered by other users and processed by the system between the time the medication order is initiated and when the order is processed. Accordingly, such systems that allow multiple users to simultaneously enter orders typically perform conflict checking at the time a medication order is processed. Although such an approach prevents the system from missing superseding orders for conflict checking, the approach presents a drawback and area of inefficiency. In particular, a user must enter all the details of an order before any conflict checking is performed. If a conflict is determined, the order may not be processed and the time taken to enter the details of the order is essentially wasted. The drawback is accentuated for cases in which a user is entering an order set, which may contain over a hundred orders and require a substantial amount of time to enter. In such cases, a user enters the details of all the orders, and conflict checking is then performed for each of the orders. If any conflicts are determined, the system may allow the user to process the orders that do not have a conflict while removing the orders having a conflict. However, such removal may disrupt the context of the order set.

Another approach to provide a static profile for conflict checking is to place a lock or reserve on a profile when a user is entering an order that will require conflict checking (i.e., a lockable order). For example, when a user initiates a medication order, the order management system will determine that the order is a lockable order and lock the profile, thereby preventing other users from entering other lockable orders while the profile is locked. By doing so, the system has a static profile for conflict checking from the time the medication order is initiated until the order is processed. If a conflict is determined, the user is notified right away, instead of being notified after already having entered the details of the order. However, such order management systems that provide profile locking also present a drawback. In particular, other users are prevented from initiating and entering details of lockable orders while the profile is locked. In addition, the users must continuously check the profile to determine when it becomes available. Accordingly, a user wishing to enter a lockable order into a locked profile must continue to check the profile to determine when the profile becomes available, obtain the lock for the profile, and then initiate his/her lockable order.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to an electronic order management system within a clinical environment that employs profile locking, requiring users to obtain a profile lock in order to perform conflict checking for lockable order actions (e.g., order actions requiring a profile lock for conflict checking). Although the system employs profile locking, the system allows users to initiate lockable order actions while the profile is locked by another user, but prevents the lockable order actions from being processed until the user obtains the profile lock. The system may monitor the profile lock and provide a notification to the user when the profile becomes available. The user may then obtain the profile lock and have the system process the lockable order action.

Accordingly, in one aspect, an embodiment of the present invention is directed to a method in a clinical computing environment for processing a lockable order action for a patient profile. The method includes receiving a command from a first user to initiate the lockable order action for the patient profile. The method also includes determining that the patient profile is locked by a second user. The method additionally includes allowing the first user to proceed with initiating the lockable order action without processing the lockable order action while the patient profile is locked. The method further includes determining that the patient profile is available and locking the patient profile for the first user. The method still further includes processing the lockable order action.

In another aspect of the invention, an embodiment is directed to another method in a clinical computing environment for processing a lockable order action for a patient profile. The method includes receiving a first command from a first user to initiate the lockable order action for the patient profile. The method also includes determining that the patient profile is locked by a second user and presenting a profile locked notification to the first user indicating that the patient profile is locked. The method further includes receiving a second command from the first user to proceed with initiating the lockable order action and to provide a notification to the first user when the patient profile becomes available. Incident to the second command, the method includes allowing the first user to proceed with initiating the lockable order action without processing the lockable order action while the patient profile is locked and providing a notification to the first user when the patient profile becomes available. The method further includes determining that the patient profile is available and presenting a profile available notification to the first user. The method still further includes receiving a third command from the first user to obtain a lock on the patient profile. Incident to the third command, the method includes locking the patient profile for the first user and processing the lockable order action.

Embodiments of the present invention further relate to allowing a user wishing to enter a lockable order action in a locked profile to initiate an instant messaging session with the user who has the profile locking. Accordingly, an embodiment of the present invention is directed to a method in a clinical computing environment for initiating an instant messaging session between a first user attempting to process a lockable order action for a patient profile and a second user having a lock on the patient profile. The method includes receiving a command from the first user to initiate the lockable order action for the patient profile. The method also includes determining that the patient profile is locked by the second user. The method further includes providing for the initiation of the instant messaging session between the first user and the second user.

BRIEF DESCRIPTION OF THE SEVERAL VIEWS OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention relate to an electronic order management system that employs profile locking but allows users to initiate lockable order actions while the profile is locked by another user. As used herein, the term "order action" refers to any type of action affecting a new or existing order in an electronic order management system, including, for example, initiating a new order, modifying an existing order, and terminating an existing order. Additionally, as used herein, the term "lockable order action" refers to any type of order action that requires a profile lock to perform conflict checking. The types of order actions that require a profile lock for conflict checking may vary within the scope of the present invention. Conversely, as used herein, the term "permissible order action" refers to any type of order action that does not require a profile lock for conflict checking. Further, it should be noted that the terms "lock" and "reserve" are used interchangeably herein.

In accordance with certain embodiments of the present invention, when a user attempts to initiate a lockable order action while the profile is locked by another user, the system presents a notification to the user indicating that the profile is locked. The user may then choose to proceed with initiating the lockable order action while the profile is locked and receive an automatic notification when the profile becomes available. Although the user may initiate the order action, the system will prevent the user from signing the lockable order action while the profile is locked. However, in cases in which the user initiates multiple order actions while the profile is locked, any permissible order actions may be signed and processed, while lockable order actions are held until a profile lock is obtained for the user. When the profile becomes available, the user may receive a notification and request the profile lock. After obtaining the profile lock, the user may choose to sign any initiated order actions. An indication may be provided of any order actions entered by other users while the profile was locked and the current user was initiating the order actions. In addition, conflict checking may be performed, and an indication may be provided if any conflicts are determined.

Embodiments of the present invention further provide computerized methods and systems for initiating an instant messaging session between a user attempting to enter a lockable order action in a locked profile and another user having the profile lock. In accordance with such embodiments, when a user attempts to initiate a lockable order action while the profile is locked by another user, the system may provide a locked profile notification. The user may then elect to initiate an instant messaging session with the user having the profile lock in order to communicate intentions, desires, and/or needs for the profile lock.

Having described a brief overview of embodiments of the invention, an exemplary operating environment will now be described. Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

Figure 1:
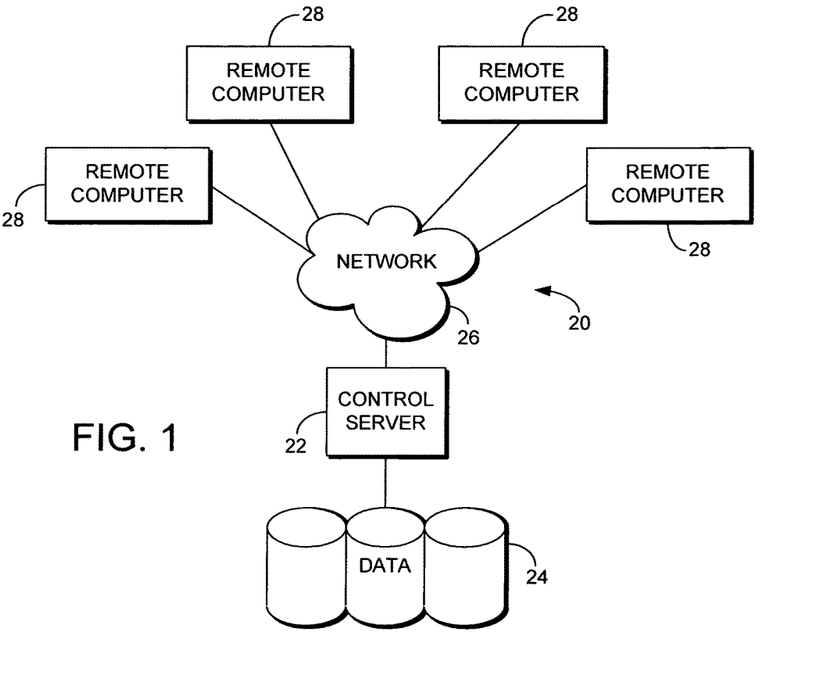
FIG. 1 is a block diagram of an exemplary computing environment suitable for use in implementing the present invention.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

As noted previously, embodiments of the present invention are directed to an electronic order management system that employs profile locking for lockable order actions but allows users to initiate lockable order actions while the profile is locked by another user. Accordingly, referring to FIG. 2A and 2B, an exemplary flow diagram is provided illustrating a method 200 for processing order actions in accordance with an embodiment of the present invention. Initially, as shown at block 202 of FIG. 2A, an order management system receives a command from a user to initiate an order action. Whether the order action comprises a lockable order action is determined at block 204. If the order action does not comprise a lockable order action, the system allows the user to proceed with the order action without acquiring a profile lock, as shown at block 206. Alternatively, if the order action is determined to comprise a lockable order action, the system determines whether the corresponding profile is currently locked by another user, as shown at block 208. In embodiments, the profile is locked by the second user automatically if the second user is creating, modifying or discontinuing orders. If the profile is not currently locked by another user, the system may lock the profile for the current user, as shown at block 210. After obtaining the profile lock, the user may then proceed with entering details of the lockable order action and having the lockable order action processed by the system, as shown at block 212. Because the user has the profile lock, the system may perform conflict checking, such as interaction checking and duplicate checking, for example, while the lockable order action is initiated, as discussed previously.

If, at block 208, it is determined that the profile is currently locked by another user, the system provides a profile locked notification to the user, as shown at block 214. In some embodiments, in conjunction with the profile locked notification, the system may allow the user to select one of any number of options, such as, for example, to proceed with initiating the lockable order action and receive a notification when the profile becomes available, to break the current profile lock, to initiate an instant messaging session with the user having the profile lock, or to cancel the initiation of the lockable order action. In the embodiment shown in FIG. 2, the user selects to initiate the lockable order action and to receive a profile available notification when the profile becomes unlocked, as shown at block 216.

Based on the user selection, the system allows the user to initiate the lockable order action, as shown at block 218. Accordingly, the user may enter details for the lockable order action, such as dosage information for a medication, for instance. In addition, the system monitors the profile lock to determine when the profile becomes available, as shown at block 220. One skilled in the art will recognize that the profile may become available in a number of ways within the scope of the present invention. For example, the profile may be manually unlocked by the user having the profile lock or the system may automatically unlock the profile, for instance, after a default time has expired. Once the profile becomes available, a profile available notification is provided to the user, as shown at block 222. In some cases, multiple users may be simultaneously initiating lockable order actions and awaiting a profile available notification. Accordingly, in some embodiments, the system may provide the profile unlocked notification to each of the users. The first user to select to obtain the profile lock is then given the profile lock. In other embodiments, a profile available notification may be provided to only one of the users based on, for example, an order in which the users initiated a lockable order action or a predetermined order of priority for the various users. In such embodiments, the system may also automatically provide the profile lock to that user.

After receiving a profile available notification, the user may obtain the profile lock, as shown at block 224. The user may then provide input to sign the lockable order action, as well as any other order actions the user has initiated, as shown at block 226 of FIG. 2B. Based on the user command, the system accesses data for the current patient profile, as shown at block 228. Based on the accessed data, the system may determine whether any new order actions were entered for the patient profile by other users while the current user was initiating any lockable order actions without the profile lock, as shown at block 230. If any new order actions were entered, a notification may be provided to the current user indicating these new order actions, as shown at block 232. In addition, the system may perform conflict checking to determine whether any conflicts are present for any lockable order actions the user is attempting to process, as shown at block 234. If any conflicts are determined, the system may provide a notification of the identified conflicts to the user, as shown at block 236. In some embodiments, the conflict notification and new order action notification may be provided in a single notification, such as in a reconciliation dialog displayed to the user. Additionally, in some embodiments, only those new order actions having conflicts with any lockable order actions being entered by the user are presented. In other embodiments, all new order actions (with or without conflicts with lockable order actions being entered by the user) are presented to the user. Further, conflict checking and new order action determination may be performed any time after the current user obtains the profile lock, including prior to the current user selecting to sign any order action. Any and all such variations are contemplated to be within the scope of embodiments of the present invention.

If no conflicts are determined for the order actions the user is attempting to process at block 234, the order actions are processed by the system, as shown at block 238. Alternatively, if a conflict is determined at block 234, the user may determine whether to proceed with processing those order actions that do not have a conflict, as shown at block 240. If the user chooses to proceed, the order actions having a conflict are removed, and the order actions that do not have a conflict are processed, as shown at block 242. If the user chooses not to proceed, the order actions are held, as shown at block 244. The user may then modify the order actions as desired.

Figure 2A:
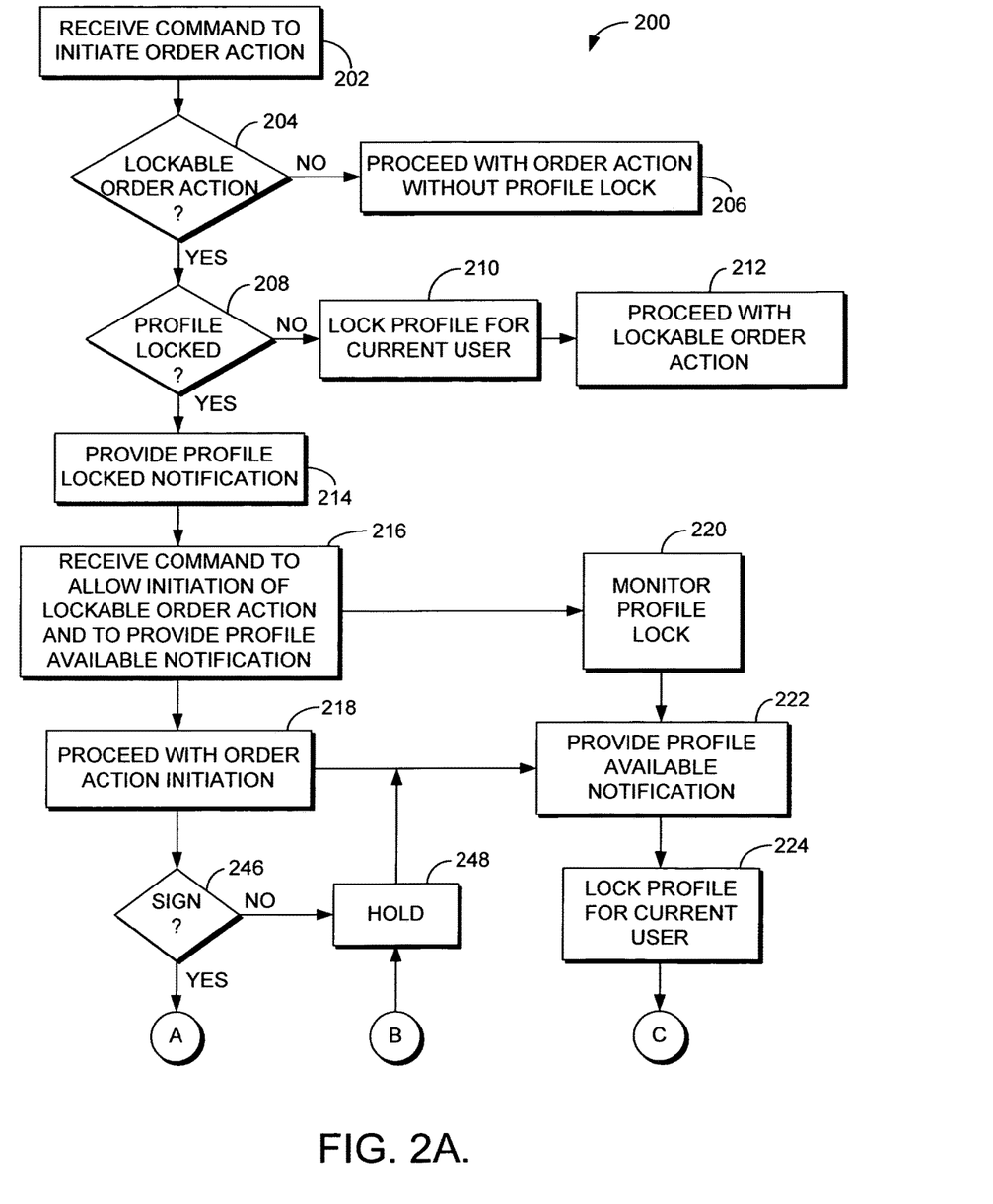
FIGS. 2A and 2B comprise a flow diagram showing an exemplary method for processing order actions in accordance with an embodiment of the present invention.
Figure 2B:
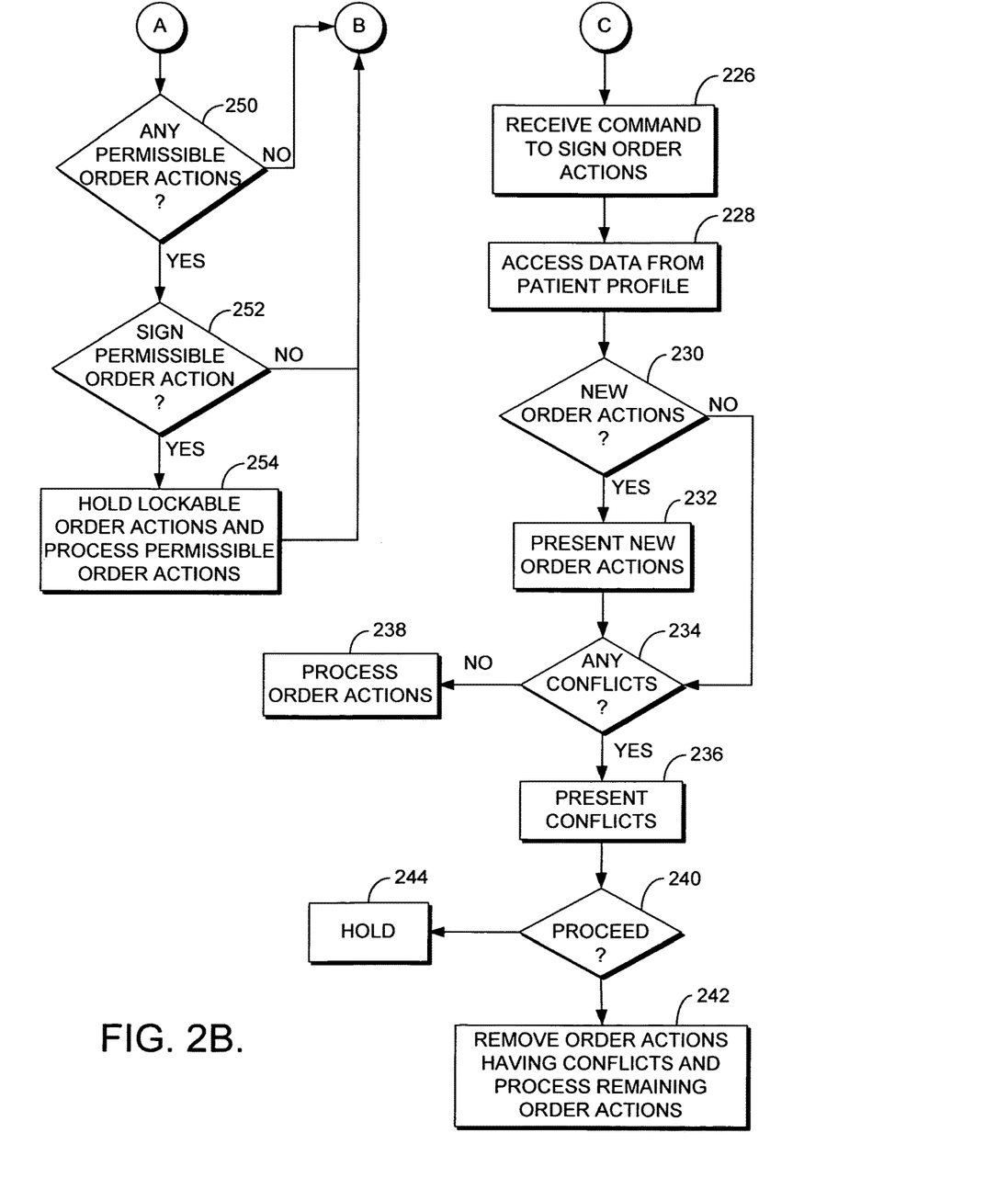

In some cases, the user may complete the details of the lockable order action before the profile becomes unlocked and attempt to sign the lockable order action, as well as any other order actions the user has initiated, as shown at block 246 of FIG. 2A. If the user chooses not to sign at block 246, the order actions are held at block 248. Alternatively, if the user elects to sign at block 246, whether any of the order actions that the user is attempting to sign is a permissible order action is determined at block 250 of FIG. 2B. If each of the order actions is a lockable order action, the system will not allow any of the order actions to be processed and will hold the order actions, as shown at block 248 of FIG. 2A. Alternatively, if any of the order actions is a permissible order action, the system will allow the user to select whether to process the permissible order actions while holding the lockable order actions, as shown at block 252 of FIG. 2B. If the user chooses not to proceed with signing the permissible order actions, all of the order actions are held at block 248 of FIG. 2A. Alternatively, if the user elects to proceed with signing the permissible order actions, the lockable order actions are held while the permissible order actions are processed, as shown at block 254 of FIG. 2B. Once the profile lock becomes available and is obtained by the user, the lockable order actions, as well as any other order actions held at block 248, may be processed as discussed above with reference to block 222 through block 244.

Figure 3:
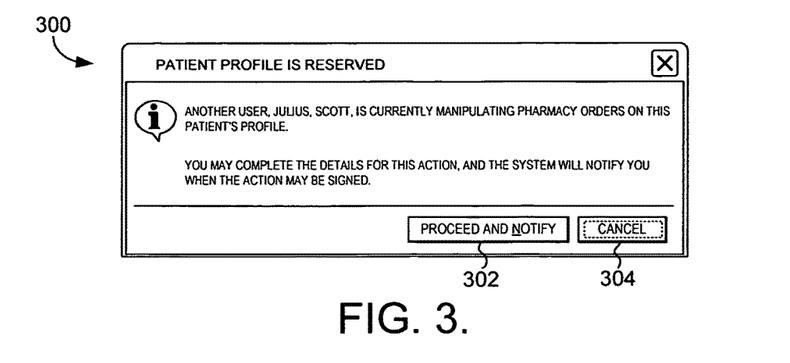
FIG. 3 is an illustrative screen display showing a profile locked notification provided if a user attempts to initiate a lockable order action for a locked profile in accordance with an embodiment of the present invention.

An exemplary profile locked notification 300 in accordance with an embodiment of the present invention is illustrated in FIG. 3. As discussed above, when a user attempts to initiate a lockable order action for a locked profile, the system may display a notification indicating to the user that the patient profile is currently locked by another user. The profile locked notification 300 may also provide information such as the user who currently has the lock and the order actions currently being manipulated for the profile by the other user. The profile locked notification 300 may further indicate to the user that details of the order action may be completed while the profile is locked, and another notification may be provided when the profile becomes available. Accordingly, the user can choose to proceed with initiating the lockable order action and to receive a notification when the profile becomes available by selecting the "Proceed and Notify" button 302. Alternatively, the user may decide not to proceed with initiating the lockable order action and may select the "Cancel" button 304.

Figure 4:
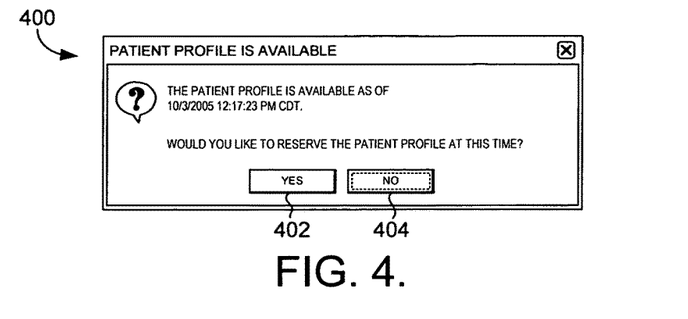
FIG. 4 is an illustrative screen display showing a profile available notification provided when a profile becomes unlocked in accordance with an embodiment of the present invention.

If a user provides input to proceed with initiating the lockable order action, a notification, such as the profile available notification 400 shown in FIG. 4, is provided to the user when the profile becomes available. The profile available notification 400 may provide information such as the date and time the profile became available. In addition, the profile available notification 400 may allow the user to attempt to lock the profile. For example, the user may select the "Yes" button 402 to request the profile lock. Alternatively, the user may not wish to lock the profile at the current time (e.g., the user may not currently have time to complete the order action) and may accordingly select the "No" button 404.

Figure 5:
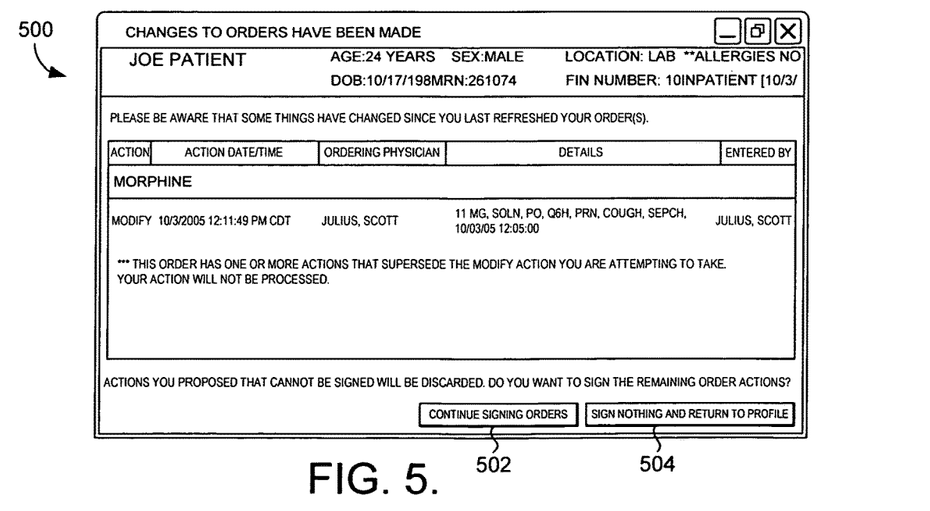
FIG. 5 is an illustrative screen display showing a dialog allowing for user indications to the system to process permissible orders while the profile is locked in accordance with an embodiment of the present invention.

As discussed previously, after the user acquires the profile lock, the system may determine if any new order actions were processed for the patient profile while the profile was locked by another user and the current user was initiating a lockable order action. In addition, the system may perform conflict checking. If any new order actions and/or conflicts are identified, a reconciliation dialog may be presented to the user, notifying the user of the new order actions and/or conflicts. FIG. 5 illustrates an exemplary reconciliation dialog 500 in accordance with an embodiment of the present invention. As noted, the reconciliation dialog 500 may indicate any new order actions that have been processed for the profile, as well as any conflicts that exist for any lockable order actions initiated by the user. If there are any order actions not having a conflict, the user may select the "Continue Signing Orders" button 502 to sign those order actions. Any order actions having a conflict are removed. Alternatively, the user may select to return to the profile by selecting the "Sign Nothing and Return to Profile" button 504. For example, the user may rather modify the order actions having conflicts and then proceed with signing all of the order actions the user has initiated.

Figure 6:
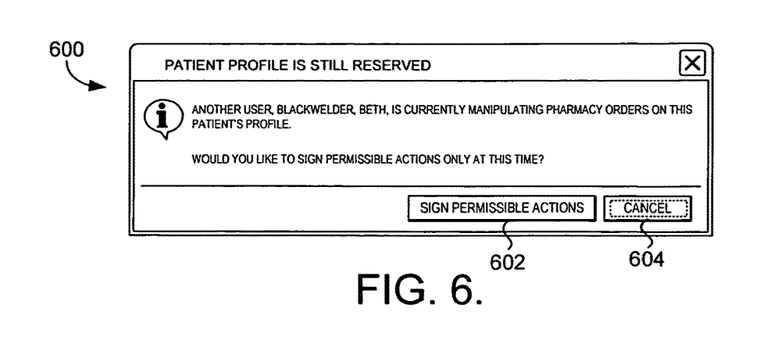
FIG. 6 is an illustrative screen display showing a reconciliation dialog in accordance with an embodiment of the present invention.

In some cases, a user working on a lockable order action while waiting for the profile lock may attempt to sign the lockable order action before the patient profile becomes available. In such cases, a notification such as the notification 600 shown in FIG. 6 may be presented to indicate that the profile is still locked. If the user is working on multiple order actions, the system may allow the user to sign any permissible order actions while holding the lockable order actions. If the user chooses to sign the permissible actions, the user may select the "Sign Permissible Actions" button 602. Otherwise, the user may choose to hold all the order actions and may select the "Cancel" button 604. The system will continue to monitor the profile lock and provide a profile available notification when the profile becomes available.

Figure 7:
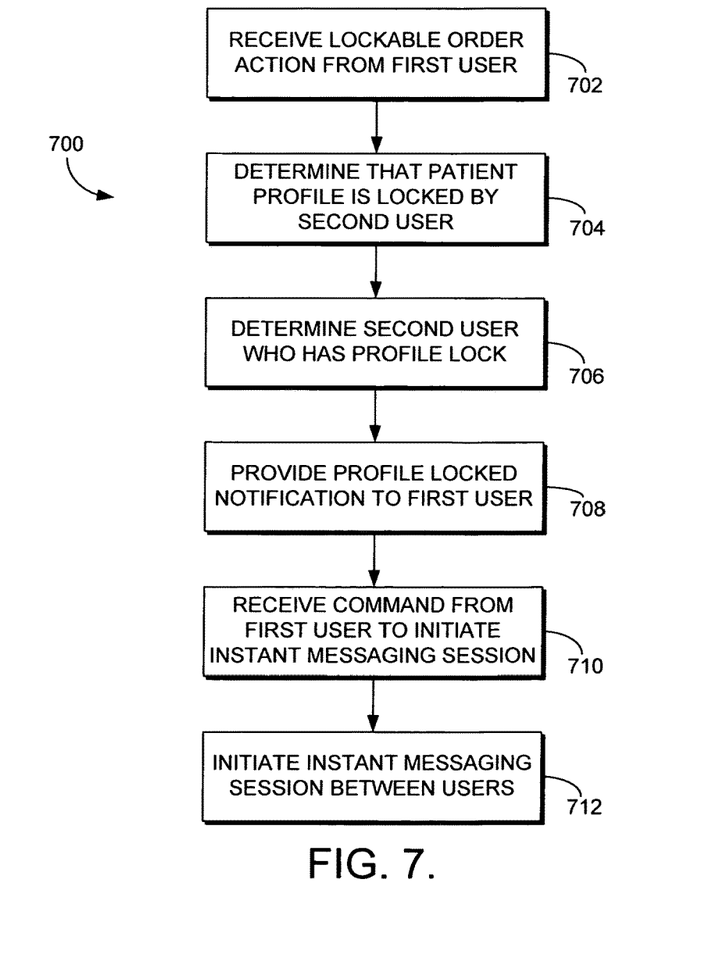
FIG. 7 is a flow diagram showing an exemplary method for initiating an instant messaging session between a user wishing to enter a lockable order and another user having a profile lock in accordance with an embodiment of the present invention.

Further embodiments of the present invention are directed towards allowing a user wishing to enter a lockable order action for a locked profile to initiate an instant messaging session with the user having the profile lock. Referring to FIG. 7, a flow diagram is provided showing a method 700 for initiating an instant messaging session between a user attempting to enter a lockable order action for a locked profile and another user having the profile lock. Initially, as shown at block 702, the system receives a command from a first user to initiate a lockable order action. The system determines that the profile is currently locked by a second user, as shown at block 704. In addition, the system determines an identity of the second user who currently has the profile lock, as shown at block 706. A profile locked notification is then provided to the first user at block 708. The notification may provide information regarding the second user having the profile lock. In addition, the notification may allow the first user to select to initiate an instant messaging session with the second user. Accordingly, the system receives a command from the first user to initiate an instant messaging session, as shown at block 710. An instant messaging session is then initiated between the two users, as shown at block 712. The users may then communicate needs for the profile lock via the instant messaging session, thereby coordinating access to the profile lock.

Figure 8:
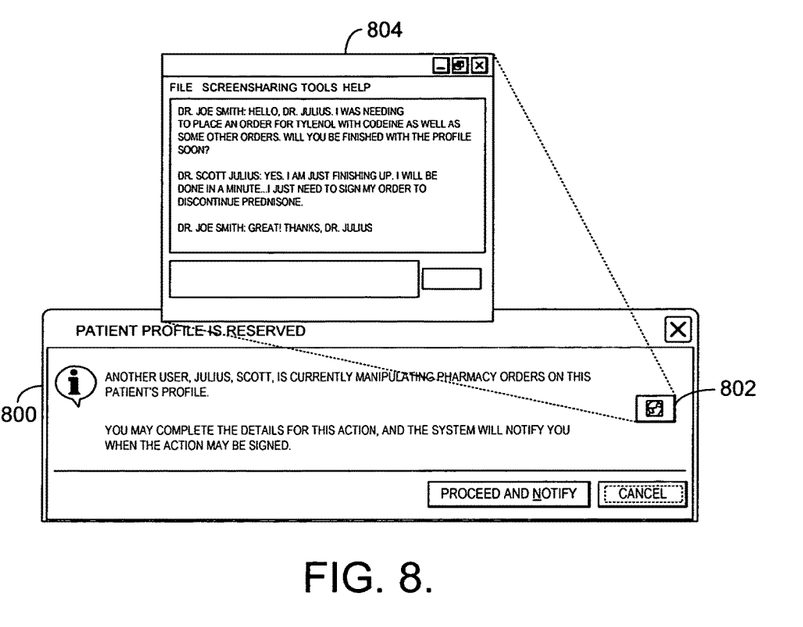
FIG. 8 is an illustrative screen display showing an instant messaging session initiated between a user attempting to enter a lockable order action and another user having a profile lock in accordance with an embodiment of the present invention.

An exemplary display is provided in FIG. 8 showing a profile locked notification 800 provided to a user attempting to enter a lockable order action in a locked profile. The profile locked notification 800 may include an instant messaging button 802 that a user may select to initiate an instant messaging session with the user having the profile lock. The user may review the information provided by the notification, including the user who currently has the profile lock, and decide to initiate an instant messaging session to attempt to gain the profile lock. After selecting the instant messaging button 802, an instant messaging window 804 is provided as shown in the exemplary display of FIG. 8. The instant messaging window 804 allows the users to enter messages and coordinate access to the patient profile for entering lockable order actions.

As can be understood, the present invention allows users to initiate lockable order actions for a patient profile that is locked by another user. The present invention further allows a user who wishes to enter a lockable order action in a locked profile to initiate an instant messaging session with the user who currently has a lock on a patient profile. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer-storage media storing computer-usable instructions that when used by a computing device, cause the computing device to perform a method in a clinical computing environment for processing a lockable order action for a patient profile, the method comprising:
   identifying that a patient profile is locked by a current user;
   receiving a command from a subsequent user to initiate an order action for the patient profile locked by the current user;
   identifying that the order action is a lockable order action because the order action requires processing a conflict check, wherein a user that requests said processing is required to possess a lock to a patient profile to which the lockable order action corresponds in order to process the conflict check;
   based on identifying that the order action is a lockable order action that requires a conflict check, providing access to the patient profile for the subsequent user to enter details of the lockable order action, wherein the access is provided to the subsequent user while the patient profile is locked by the current user and without processing the conflict check because the patient profile is locked by the current user;
   processing one or more permissible order actions entered by the subsequent user while the patient profile is locked by the current user, wherein processing the one or more permissible order actions does not require a conflict check and is performed without processing the conflict check for the lockable order action;
   determining that the patient profile is available such that the patient profile is not locked by the current user;
   locking the patient profile to the subsequent user; and
   in response to locking the patient profile to the subsequent user, processing the lockable order action by performing the conflict check relative to other order actions while the patient profile is locked to the subsequent user.

2. The computer-storage media of claim 1, wherein the lockable order action comprises one or more of an action initiating a new medication order, an action modifying an existing medication order, and an action terminating an existing medication order.

3. The computer-storage media of claim 1, further comprising incident to identifying that the order action is a lockable order action because the order action requires processing a conflict check, presenting a profile locked notification to the subsequent user indicating that the patient profile is locked.

4. The computer-storage media of claim 3, wherein the method further includes incident to presenting the profile locked notification, receiving a second command from the subsequent user to provide a profile available notification when the patient profile becomes available.

5. The computer-storage media of claim 1, further comprising incident to determining that the patient profile is available such that the patient profile is not locked by the current user, providing a profile available notification to the subsequent user.

6. The computer-storage media of claim 1, wherein locking the patient profile to the subsequent user comprises receiving a second command from the subsequent user to lock the patient profile.

7. The computer-storage media of claim 1, wherein performing the conflict check for the lockable order action comprises performing at least one of interaction checking and duplicate checking for the lockable order action.

8. The computer-storage media of claim 1, wherein processing the lockable order action comprises presenting a reconciliation dialog.

9. The computer-storage media of claim 8, wherein the reconciliation dialog comprises information regarding one or more of:
   an order action entered in the patient profile since receiving the command from the subsequent user to initiate the lockable order action, and
   a conflict between the lockable order action and an order in the patient profile.

10. The computer-storage media of claim 8, wherein the reconciliation dialog is presented incident to locking the patient profile to the subsequent user.

11. The computer-storage media of claim 8, wherein processing the lockable order action further comprises receiving a second command from the subsequent user to sign the lockable order action.

12. The computer-storage media of claim 11, wherein the reconciliation dialog is presented incident to receiving the second command from the subsequent user to sign the lockable order action.

13. A system operating in a networking environment having logical connections to one or more remote computer devices, the system comprising:
a server that operates to:
identify that a patient profile is locked to a current user;
receive a first command from a subsequent user at a remote computing device to initiate an order action for the patient profile that is locked to the current user;
identify that the order action is a lockable order action because the order action requires processing a conflict check, wherein said processing a conflict check requires user possession of a lock to a patient profile to which the lockable order action corresponds in order to process the conflict check;
communicate a profile locked notification to the subsequent user indicating that the patient profile is locked, the profile lock notification to be presented at the remote computing device;
receive a second command from the subsequent user to proceed with initiating the lockable order action and to provide a notification to the subsequent user when the patient profile becomes available;
incident to the second command, provide access to the patient profile for the subsequent user to enter details of the lockable order action, wherein access is provided to the subsequent user while the patient profile is locked to the current user and without processing the conflict check because the patient profile is locked to the current user;
receive a third command from the subsequent user to process one or more permissible order actions not requiring a conflict check and not process the conflict check for the initiated lockable order action because the patient profile is locked to the current user;
determine that the patient profile is not locked to the current user and the patient profile is available;
communicate a profile available notification to the subsequent user, the profile available notification to be presented at the remote computing device;
receive a fourth command from the subsequent user to lock the patient profile to the subsequent user;
incident to the fourth command, lock the patient profile to the subsequent user; and
in response to locking the patient profile to the subsequent user, process the initiated lockable order action and perform the conflict check of the initiated lockable order action with other lockable order actions.

14. One or more computer-storage media storing computer-usable instructions that when used by a computing device, cause the computing device to perform a method in a clinical computing environment for initiating an instant messaging session between a subsequent user attempting to process a lockable order action for a patient profile and a current user having a lock on the patient profile, the method comprising:
identifying that a patient profile is locked to a current user;
receiving a command from the subsequent user to initiate an order action for the patient profile that is locked to the current user;
identifying that the order action is a lockable order action because the order action requires processing a conflict check, wherein processing a conflict check requires user possession of a lock to a patient profile to which the lockable order action corresponds in order to process the conflict check;
providing for the initiation of the instant messaging session between the subsequent user and the current user;
initiating the lockable order action by providing access to the patient profile for the subsequent user to enter details of the lockable order action, wherein the access is provided to the subsequent user while the patient profile is locked to the current user and without processing the conflict check because the patient profile is locked to the current user;
processing one or more permissible order actions not requiring a conflict check and entered by the subsequent user without processing the conflict check for the initiated lockable order action;
determining that the patient profile is not locked to the current user and is available;
locking the patient profile to the subsequent user; and
in response to locking the patient profile to the subsequent user, processing the lockable order action by performing the conflict check relative to other order actions.

15. The computer-storage media of claim 14, further comprising incident to identifying that the order action is a lockable order action because the order action requires processing a conflict check, presenting a profile locked notification to the subsequent user indicating that the patient profile is locked.

16. The computer-storage media of claim 15, wherein the profile locked notification comprises information regarding at least one of the current user, and a current order action being entered by the current user.

17. The computer-storage media of claim 15, wherein the profile locked notification further provides for receiving a second command from the subsequent user to initiate the instant messaging session between the subsequent user and the current user.

18. The computer-storage media of claim 14, wherein providing for the initiation of the instant messaging session comprises:
receiving a second command from the subsequent user to initiate the instant messaging session between the subsequent user and the current user; and
incident to the second command, initiating the instant messaging session between the subsequent user and the current user.

19. The computer-storage media of claim 14, wherein the patient profile is locked to a current user when the current user is entering, modifying or terminating one or more lockable order actions for the patient.

20. The system of claim 13, wherein the lockable order action comprises one or more of:
an action initiating a new medication order,
an action modifying an existing medication order, and
an action terminating an existing medication order.

* * * * *

UNITED STATES PATENT AND TRADEMARK OFFICE
CERTIFICATE OF CORRECTION

PATENT NO.         : 10,339,617 B2
APPLICATION NO.    : 11/345565
DATED              : July 2, 2019
INVENTOR(S)        : Christopher Nessinger et al.

Page 1 of 1

It is certified that error appears in the above-identified patent and that said Letters Patent is hereby corrected as shown below:

On the Title Page

Item (73) Assignee: Please remove "Innovations" and replace with --Innovation--.

Column 02, Other Publications, Line 03: Please remove "chap 12/chap 12.html" and replace with --chap12/chap12.html--.

Signed and Sealed this
Twentieth Day of August, 2019

Andrei Iancu
*Director of the United States Patent and Trademark Office*